(12) United States Patent
Mailland et al.

(10) Patent No.: US 10,172,811 B2
(45) Date of Patent: *Jan. 8, 2019

(54) TOPICAL ANTIFUNGAL COMPOSITION FOR TREATING ONYCHOMYCOSIS

(71) Applicant: Polichem S.A., Luxembourg (LU)

(72) Inventors: Federico Mailland, Lugano (CH); Michela Legora, Appiano Gentile (IT); Daniela Ceriani, Besano (IT); Giuliana Iob, Lugaggia (CH)

(73) Assignee: Polichem SA, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 14/765,964

(22) PCT Filed: Jan. 23, 2014

(86) PCT No.: PCT/EP2014/051288
§ 371 (c)(1),
(2) Date: Aug. 5, 2015

(87) PCT Pub. No.: WO2014/122024
PCT Pub. Date: Aug. 4, 2014

(65) Prior Publication Data
US 2015/0366822 A1    Dec. 24, 2015

Related U.S. Application Data

(60) Provisional application No. 61/781,560, filed on Mar. 14, 2013, provisional application No. 61/761,953, filed on Feb. 7, 2013.

(51) Int. Cl.
| *A61K 9/00* | (2006.01) |
| *A61K 47/10* | (2017.01) |
| *A61K 47/36* | (2006.01) |
| *A61K 31/137* | (2006.01) |

(52) U.S. Cl.
CPC .......... *A61K 31/137* (2013.01); *A61K 9/0014* (2013.01); *A61K 47/10* (2013.01); *A61K 47/36* (2013.01)

(58) Field of Classification Search
CPC .... A61K 9/0014; A61K 31/137; A61K 47/10; A61K 47/36
See application file for complete search history.

(56) References Cited

U.S. PATENT DOCUMENTS

| 3,883,545 A | 5/1975 | Lohaus et al. |
| 4,202,894 A | 5/1980 | Pfiffner |
| 4,755,534 A | 7/1988 | Stuetz |
| 4,772,690 A | 9/1988 | Lang et al. |
| 4,780,310 A | 10/1988 | Lang et al. |
| 4,822,598 A | 4/1989 | Lang et al. |
| 4,923,977 A | 5/1990 | Lang et al. |
| 4,946,870 A | 8/1990 | Partain, III et al. |
| 4,954,619 A | 9/1990 | Lang et al. |
| 4,957,730 A | 9/1990 | Bohn et al. |
| 5,120,530 A | 6/1992 | Ferro et al. |
| 5,264,206 A | 11/1993 | Bohn et al. |
| 5,346,692 A | 9/1994 | Wohlrab et al. |
| 5,391,367 A | 2/1995 | DeVincentis et al. |
| 5,681,849 A | 10/1997 | Richter et al. |
| 5,696,164 A | 12/1997 | Sun et al. |
| 5,814,305 A | 9/1998 | Laugier et al. |
| 5,856,355 A | 1/1999 | Richter et al. |
| 5,866,105 A | 2/1999 | Richter et al. |
| 5,965,111 A | 10/1999 | Ellingson et al. |
| 6,005,001 A | 12/1999 | Richter et al. |
| 6,007,798 A | 12/1999 | Bohn et al. |
| 6,121,314 A | 9/2000 | Richter et al. |
| 6,143,793 A | 11/2000 | Laugier et al. |
| 6,159,977 A | 12/2000 | Reeves |
| 6,162,429 A | 12/2000 | Wallis et al. |
| 6,214,360 B1 | 4/2001 | Richter et al. |
| 6,224,887 B1 | 5/2001 | Samour et al. |
| 6,306,375 B1 | 10/2001 | Ellingson et al. |
| 6,319,509 B1 | 11/2001 | Richter et al. |
| 6,455,592 B1 | 9/2002 | Laugier et al. |
| 7,033,578 B2 * | 4/2006 | Mailland ............... A61K 8/42 424/401 |
| 7,462,362 B2 | 12/2008 | Kepka et al. |

(Continued)

FOREIGN PATENT DOCUMENTS

| AU | 1147092 A | 9/1992 |
| AU | 1705892 B | 11/1992 |

(Continued)

OTHER PUBLICATIONS

Ajit, et al., "Terbinafine-Associated Hepatotoxicity," Am.J Med. Sciences, May 2003, vol. 325, No. 5, pp. 292-295.
Baran, et al., "An innovative water-soluble biopolymer improves efficacy of ciclopirox nail lacquer in the management of onychomycosis," JEADV, 2009, pp. 1-9.
Baran, et al., "Epidemology," Onychomycosis, the current approach to diagnosis and therapy, 1999, pp. 6-9.
Bulgheroni, et al., "Effect of an innovative terbinafine nail solution (P3058) on in vitro nail experimental infections," (2013) P6940, American Academy of Dermatology Annual Meeting, 9 pgs.
Declaration of Federico Mailland Under 37 CFR 1.132 dated May 22, 2004, filed in U.S. Appl. No. 10/297,345.
EU Clinical Trials Register, 2009, 8 pgs.

(Continued)

*Primary Examiner* — Michael B. Pallay
(74) *Attorney, Agent, or Firm* — Finnegan, Henderson, Farabow, Garrett & Dunner, LLP

(57) ABSTRACT

A topical antifungal composition for treating onychomycosis includes a terbinafine and/or a pharmaceutically acceptable salt thereof in an amount of from 9% to 11% by weight of the composition, a hydroxypropyl chitosan in an amount of from 0.1% to 0.6% by weight of the composition, water in an amount of from 10.0% to 40.0% by weight of the composition, and a $C_1$-$C_4$ alkanol in an amount of from 60% to 80% by weight of the composition.

4 Claims, 2 Drawing Sheets

(56) References Cited

U.S. PATENT DOCUMENTS

| | | | |
|---|---|---|---|
| 7,820,720 | B2 | 10/2010 | Cevc et al. |
| 8,697,753 | B1* | 4/2014 | Mailland ............ A61K 9/0014 424/405 |
| 9,107,877 | B2* | 8/2015 | Mailland ............ A61K 9/0014 |
| 2001/0046478 | A1 | 11/2001 | Bohn et al. |
| 2003/0118655 | A1 | 6/2003 | Kundel |
| 2006/0067898 | A1 | 3/2006 | Kepka et al. |
| 2006/0120977 | A1 | 6/2006 | Friedman et al. |
| 2008/0261986 | A1 | 10/2008 | Friden et al. |
| 2010/0048724 | A1 | 2/2010 | Birnbaum et al. |
| 2010/0086504 | A1* | 4/2010 | Cevc ................. A61K 9/0014 424/61 |
| 2010/0128612 | A1 | 5/2010 | Qian et al. |
| 2012/0128612 | A1 | 5/2012 | Lenn et al. |
| 2012/0309843 | A1 | 12/2012 | Buyuktimkin et al. |

FOREIGN PATENT DOCUMENTS

| | | |
|---|---|---|
| BR | 9200786 A | 11/1992 |
| CA | 2002404 A1 | 5/1990 |
| CA | 1283054 C | 4/1991 |
| CA | 1305060 C | 7/1992 |
| CA | 2062341 C | 9/1992 |
| CA | 2245693 C | 8/1997 |
| CA | 2069153 C | 12/2002 |
| CA | 2343284 C | 11/2008 |
| CN | 1324607 A | 12/2001 |
| DE | 4108664 A1 | 9/1992 |
| DE | 10061801 A1 | 7/2001 |
| EP | 0024587 A1 | 3/1981 |
| EP | 0055396 A1 | 7/1982 |
| EP | 0055397 B1 | 8/1984 |
| EP | 0115574 A1 | 8/1984 |
| EP | 0192932 A1 | 9/1986 |
| EP | 0198246 A1 | 10/1986 |
| EP | 0224045 A2 | 6/1987 |
| EP | 0226984 A1 | 7/1987 |
| EP | 0243334 A1 | 10/1987 |
| EP | 0277322 A1 | 8/1988 |
| EP | 0368253 A2 | 5/1990 |
| EP | 0298271 B1 | 1/1992 |
| EP | 0300234 B1 | 5/1992 |
| EP | 0503988 A1 | 9/1992 |
| EP | 0504754 A1 | 9/1992 |
| EP | 0247142 B1 | 1/1993 |
| EP | 0389778 B1 | 5/1994 |
| EP | 0515312 B1 | 8/1996 |
| EP | 0565072 B1 | 3/1997 |
| EP | 0777457 A1 | 6/1997 |
| EP | 0792137 A1 | 9/1997 |
| EP | 0806935 A2 | 11/1997 |
| EP | 0711140 B1 | 9/1999 |
| EP | 0985408 A2 | 3/2000 |
| EP | 0879052 B1 | 12/2000 |
| EP | 1083862 A2 | 3/2001 |
| EP | 1085850 A1 | 3/2001 |
| EP | 0983037 B1 | 5/2003 |
| EP | 1150655 B1 | 9/2003 |
| EP | 1138314 A3 | 1/2004 |
| EP | 1069898 B1 | 5/2004 |
| EP | 1071413 B1 | 6/2004 |
| EP | 1491202 A1 | 12/2004 |
| EP | 1143950 B1 | 3/2005 |
| EP | 1130964 B1 | 11/2005 |
| EP | 1958638 A1 | 8/2008 |
| EP | 1958639 A1 | 8/2008 |
| EP | 1545429 B1 | 12/2010 |
| EP | 1257248 B1 | 10/2011 |
| FR | 2761886 B1 | 5/2000 |
| JP | S61192701 A | 8/1986 |
| JP | S6436602 A | 2/1989 |
| JP | H02196728 A | 8/1990 |
| JP | H0585929 A | 4/1993 |
| JP | H05148136 A | 6/1993 |
| JP | H0564924 B2 | 9/1993 |
| JP | H069342 A | 1/1994 |
| JP | H06211651 A | 8/1994 |
| JP | H10152433 A | 6/1998 |
| JP | H10226639 A | 8/1998 |
| JP | 2951725 B2 | 9/1999 |
| JP | 2000504674 A | 4/2000 |
| JP | 2001316247 A | 11/2001 |
| JP | 2001523273 A | 11/2001 |
| JP | 2002053462 A | 2/2002 |
| JP | 2002524495 A | 8/2002 |
| JP | 2008-504359 | 2/2008 |
| JP | 2010-518130 | 5/2010 |
| JP | 5339152 B2 | 11/2013 |
| RU | 2245715 C2 | 2/2005 |
| WO | 8605976 A1 | 10/1986 |
| WO | 8702580 A1 | 5/1987 |
| WO | 8805790 A1 | 8/1988 |
| WO | 8806884 A1 | 9/1988 |
| WO | 9216185 A1 | 10/1992 |
| WO | 9415591 A1 | 7/1994 |
| WO | 9503775 A1 | 2/1995 |
| WO | 9611710 A1 | 4/1996 |
| WO | 9619186 A1 | 6/1996 |
| WO | 9623479 A2 | 8/1996 |
| WO | 9627374 A1 | 9/1996 |
| WO | 9636311 A1 | 11/1996 |
| WO | 9725962 A1 | 7/1997 |
| WO | 9728790 A1 | 8/1997 |
| WO | 9939680 A1 | 8/1999 |
| WO | 9947140 A1 | 9/1999 |
| WO | 9949835 A1 | 10/1999 |
| WO | 9953913 A1 | 10/1999 |
| WO | 9956705 A2 | 11/1999 |
| WO | 0007627 A2 | 2/2000 |
| WO | 0015202 A2 | 3/2000 |
| WO | 0028821 A1 | 5/2000 |
| WO | 0047177 A1 | 8/2000 |
| WO | 0113955 A1 | 3/2001 |
| WO | 0143713 A2 | 6/2001 |
| WO | 0149283 A1 | 7/2001 |
| WO | 0160325 A1 | 8/2001 |
| WO | 0166145 A1 | 9/2001 |
| WO | 0207683 A1 | 1/2002 |
| WO | 0211764 A2 | 2/2002 |
| WO | 2004010952 A2 | 2/2004 |
| WO | 2005011565 A2 | 2/2005 |
| WO | WO 2005/013955 A2 | 2/2005 |
| WO | 2005105072 A2 | 11/2005 |
| WO | WO 2006/003492 A2 | 1/2006 |
| WO | 2007042682 A1 | 4/2007 |
| WO | 2008098869 A2 | 8/2008 |
| WO | WO 2008/098634 A1 | 8/2008 |
| WO | WO2008/098871 A2 | 8/2008 |
| WO | 2011073392 A1 | 6/2011 |
| WO | WO 2011/080264 A1 | 7/2011 |
| WO | 2012013366 A2 | 2/2012 |
| ZA | 9201706 A | 11/1992 |

OTHER PUBLICATIONS

European Pharmacopoeia 7.0, 2.2.2 "Degree of Coloration of Liquids," 2008, pp. 22-24.

European Pharmacopoeia 7.0, 2.2.9 Capillary Viscometer Method, 2008, pp. 27-28.

German Standard, DIN 55_945, Dec. 1998, with English translation of Scope of Application, 19 pgs.

Hartmane, et al., "Evaluation of safety profile, pharmacokinetics and clinical benefit of an innovative terbinafine transungual solution (P-3058): a phase I, study in patients with mild-to-moderate distal subungual onychomycosis," (2013) P6322, American Academy of Dermatology Annual Meeting, 11 pgs.

Iorizzo, M. et al., "An innovative terbinafine transungual solution (P-3058): dose finding investigation on clinical benefit in patients affected by mild-to-moderate distal toe onychomycosis," (2013) P6403, American Academy of Dermatology Annual Meeting, 10 pgs.

(56) References Cited

OTHER PUBLICATIONS

Mailland, et al., "Antimycotic activity and penetration through bovine hoof membranes of an innovative terbinafine nail solution (P3058)," (2013) P6907, American Academy of Dermatology Annual Meeting, 9 pgs.

Marty, et al., "Treatment costs of three nail lacquers used in onychomycosis," J.Derm.Treatment, 2005, Vo. 16, pp. 299-307.

Monti, et al.. "Terbinafine nail solutions for topical treatment of onychomycosis: in vitro study on penetration/retention through and into keratin membranes." (2013) P6881. American Academy of Dermatology Annual Meeting. 9 pgs.

Reinel, "Topical Treatment of Onychomycosis with Amorolfine 5% Nail Lacquer: Comparative Efficacy and Tolerability of Once and Twice Weely Use," Dermatology, 1992, vol. 184(Suppl 1), pp. 21-24.

Schalka, et al., "Comparative clinical evaluation of efficacy and safety of a formulation containing cicloprirox 8% in the form of a therapeutic nail lacquer in two different posologies for the treatment of onychomycosis of the toes," An Bras Dermatol, 2012, vol. 87(1), pp. 19-25.

Slordal, et al., "Heart Failure Induced by Non-Cardiac Drugs," Drug Safety, 2006, vol. 29(7), pp. 567-586.

Tosti, et al., "Patients at risk of onychomycosis—risk factor indentification and active prevention," JEADV, 2005, vol. 19(Suppl. 1), pp. 13-16.

Loo, Daniel S., Onychomycosis in the elderly: drug treatment options, Drugs Aging (2007) pp. 293-302, vol. 24, No. 4.

Tanuma, H. et al., Usefulness of 1% terbinafine HCI (Lamisil) cream for hyperkeratotic-type tinea pedis and its ransfer into the horny layer, Mycoses (2000) pp. 417-432, vol. 43, No. 11-12.

Bohn et al., "Dermatopharmacology of ciclopirox nail lacquer topical solution 8% in the treatment of onychomycosis," Journal of the American Academy of Dermatology, vol. 43, No. 4, Oct. 2003, pp. S57-S69.

European Commission Enterprise Directorate-General, "Excipients in the Label and Package Leaflet of Medicinal Products for Human Use," Guidelines, Medicinal Products for Human Use, Safety, Environment and Information, vol. 3B, Rev. 1, Jul. 2003, 18 pages.

Gupta et al., "Ciclopirox nail lacquer and podiatric practice," Journal of the American Podiatric Medical Association, vol. 90, No. 10, Nov. 2000, pp. 502-507.

Gupta et al., "Ciclopirox 8% Nail Lacquer in the Treatment of Onychomycosis of the Toenails in the United States," Journal of the American Podiatric Medical Association, vol. 90, No. 10, Nov./Dec. 2000, pp. 495-501.

Gupta et al., "Ciclopirox nail lacquer topical solution 8% in the treatment of toenail onychomycosis," Journal of the American Academy of Dermatology, vol. 43, No. 4, Oct. 2000, pp. S70-S80.

Gupta et al., "Therapies for the treatment of onychomycosis," Clinics in Dermatology, vol. 31, 2013, pp. 544-554.

Mailland et al., "Antimycotic activity of subungual fluids as a proof of in vitro efficacious nail permeation by antimycotic nail lacquers," Journal of Investigative Dermatology, vol. 127, Supp. 2, Oct. 1, 2007, p. S22.

Monti et al., "Hydrosoluble medicated nail lacquers: in vitro drug permeation and corresponding antimycotic activity," British Journal of Dermatology, vol. 162, No. 2, Jan. 1, 2010, pp. 311-317.

Monti et al., "In Vitro Transungual Permeation of Ciclopirox from a Hydroxypropyl Chitosan-Based, Water-Soluble Nail Lacquer," Drug Development and Industrial Pharmacy, vol. 31, 2005, pp. 11-17.

"Penlac Nail Lacquer, Topical Solution (Dermik)," Medical Economics, 2002, 7 pages.

Sparavigna et al., "Physical and microbiological properties of a new nail protective medical device," Journal of Plastic Dermatology, vol. 4, No. 1, Jan. 1, 2008, pp. 5-12.

Subissi et al., "Ciclopirox: Recent Nonclinical and Clinical Data Relevant to its Use as a Topical Antimycotic Agent," Drugs, vol. 70, No. 16, 2010, pp. 2133-2152.

International Search Report dated Apr. 25, 2014 for Intl. App. No. PCT/EP2014/051288, from which the instant application is based, 6 pgs.

Elewski, B.E. et al., "Efficacy, safety and tolerability of topical terbinafine nail solution in patients with mild-to-moderate toenail onychomycosis: results from three randomized studies using double-blind vehicle-controlled and open-label active controlled designs," Journal of the European Academy of Dermatology and Venereology, vol. 27, No. 3, Mar. 2013.

Gupta, A, "Terbinafine nail solution in onychomycosis patients: Terbinafine pharmacokinetic profile and initial clinical efficacy and safety," Journal of the American Academy of Dermatology, vol. 60, No. 3, Mar. 2009.

Ghannoun, Mahmoud A. et al., "Determination of the efficacy of terbinafine hydrochloride nail solution in the topical treatment of dermatophytosis in a guinea pig model," MYCOSES, vol. 52, No. 1, Jan. 2009.

Shemer, A., "Update: medical treatment of onychomycosis," Dermatologic Therapy, vol. 25, No. 6, Nov. 2012.

\* cited by examiner

TOPICAL ANTIFUNGAL COMPOSITION FOR TREATING ONYCHOMYCOSIS

RELATED APPLICATIONS

This application is a 35 U.S.C. 371 national stage filing from International Application No. PCT/EP2014/051288, filed Jan. 23, 2014, which claims priority to U.S. Provisional Patent Application No. 61/781,560 filed Mar. 14, 2013 and U.S. Provisional Patent Application No. 61/761,953 filed Feb. 7, 2013, the teachings of each of which are incorporated herein by reference.

The present invention is directed to a nail lacquer consisting essentially of terbinafine as an antimycotic agent, hydroxypropyl chitosan as film forming agent, water and a lower alkanol as solvents. The invention is also directed to a method for treating onychomycosis by topically administering such a nail lacquer to a patient in need of such a treatment.

BACKGROUND OF THE INVENTION

Onychomycosis is an infection of the nails which represents the most common nail disease worldwide. At the beginning of the past century this fungal infection was still considered as very rare, but its prevalence increased dramatically during the last decades of the century, reaching very high rates in the US (up to 14% of the general population) and in the EU (near 30% of selected populations) (Baran R, Hay R, Haneke E, Tosti A (Eds), Epidemiology. In: Onychomycosis—the current approach to diagnosis and therapy. London, Martin Dunitz, 1999: pp. 6-9). Presently, onychomycosis represents approximately 50% of all nail disorders. It is a fungal disease of the nail mostly caused by dermatophytes, such as *Trichophyton rubrum*, *Trichophyton mentagrophytes* and *Epidermophyton floccosum*, and is far more common on the toenails than on the fingernails.

Both genders appear to be equally affected. Onychomycosis may occur at any age but it is rare prior to puberty, and an increased incidence has been reported in the elderly population. Risk factors for onychomycosis are diabetes, nail psoriasis, hyperhidrosis, impaired peripheral circulation, nail trauma, tinea pedis and immunodeficiency (Tosti A, Hay R, Arenas-Guzmán R, Patients at risk of onychomycosis—risk factor identification and active prevention. J Eur Acad Dermatol Veneorol, 2005, 19:13-16).

The pharmacological treatment of this difficult to eradicate and often recurring disease is done by oral terbinafine, which is actually considered as the golden standard for onychomycosis worldwide, and is reported to achieve a complete cure in 38% of patients. Terbinafine is an antifungal agent provided with a strong activity on dermatophytes and molds. Commercial products containing terbinafine are worldwide available as 250 mg tablets, for treatment of onychomycosis. Standard dosage is one tablet a day orally administered for 12 weeks.

Itraconazole and fluconazole are reportedly less effective. None of those drugs, terbinafine, itraconazole or fluconazole, is devoid of rare but serious, sometimes fatal adverse events (Ajit C, Suvannasankha A, Zaeri N, Munoz S J, Terbinafine-associated hepatotoxicity. Am J Med Sci. 2003; 325:292-5; Slørdal L, Spigset O. Heart failure induced by non-cardiac drugs. Drug Saf. 2006; 29:567-86).

It is unacceptable that a patient risks life-threatening adverse reactions from a treatment of nail infections. For this reason topical treatments, including ciclopirox, amorolphine and tioconazole, are also available, although their effectiveness is even lower. Among topical treatments, the most effective is ciclopirox in a specifically designed nail formulation, which achieves about 13% of complete cure and almost 30% of responders after a 48 weeks of daily treatment followed by a 12-week follow up without treatment (Baran R, Tosti A, Hartmane I et al. An innovative water soluble biopolymer improves efficacy of ciclopirox nail lacquer in the management of onychomycosis. J Eur Acad Dermatol Veneorol, 2009, 23:773-781).

A large medical need is still present in the management of onychomycosis, in order to find treatments able to improve the rate of effectiveness and at the same time to decrease the risk of toxicity. One of the most evident things is that with oral treatments the patient is systemically exposed to an enormous quantity of the drug (21,000 mg per patient in the case of terbinafine) while less than $1/1,000$ is the quantity of the drug which actually reaches the site of action, i.e. the nails. If there is the possibility to allow a direct application to the site of action, the systemic exposure, and consequently the intrinsic toxicity of the treatment, would be dramatically reduced, while the effectiveness should be maintained.

Attempts to formulate terbinafine in a topical composition to be applied directly on the affected areas are known in the art.

EP0515312 discloses compositions suitable to application on the nails containing terbinafine formulated in water insoluble polymeric film forming agents from the group of polyvinyl acetate or acrylic- and methacrylic-acid alkyl ester copolymerisates with quaternary ammonium groups or methylvinylether-maleic acid monoalkyl ester copolymerisates. No information on the real efficacy of those compositions was made available, though the fact that no commercial product having been developed from that teaching over 20 years later, may reasonably lead to conclude that no efficacy is to be expected from the matter disclosed herein. US2012/0128612A1 discloses compositions effective for application to nails comprising at least one volatile solvent, at least one film forming substance and at least one pyrimidone derivative with antifungal activity, where terbinafine may be optionally added to the composition as additional active ingredient. U.S. Pat. No. 5,681,849 discloses how to improve the dissolution of the active ingredient terbinafine and to improve spreadability by using a water soluble or water miscible nonionic surfactant. The disadvantage of such a composition is that it appears more suitable to application on skin than on nails, as it would be difficult to maintain the composition for a long time on the nail surface. U.S. Pat. No. 7,462,362B2 discloses an antifungal nail coat suitable to improve terbinafine penetration through the nail plate. Unfortunately, a nail lacquer containing 10% of terbinafine in the nail coat according to that invention was devoid of any efficacy in comparison to a placebo when applied daily for 48 weeks onto the nail surface of patients with onychomycosis, with rate of cure not overcoming 2.2% of patients daily treated by 48 weeks (Elewski B, Ghannoum M A, Mayser P et al. Efficacy, safety and tolerability of topical terbinafine nail solution in patients with mild-to-moderate toenail onychomycosis: results from three randomized studies using double-blind vehicle-controlled and open-label active-controlled designs. J Eur Acad Dermatol Veneorol, 2011, DOI: 10.1111/j.1468-3083.2011.04373.x). US2008/0261986A1 discloses a formulation suitable for iontophoresis comprising terbinafine, solvents and a penetration enhancer from the group of benzoic acid, oleic acid, salycilic acid, cysteine, acetylcisteine and urea. WO02/

11764A2 discloses how to improve nail penetration of terbinafine by making several holes in the nail plate by means of a laser, in order to improve the terbinafine permeation from a composition to be put onto the nail surface. None of the aforementioned prior art was able to demonstrate effectiveness from the proposed compositions and technologies, moreover the last two appear as unfeasible in clinical setting from the practical point of view. WO02/07683A1 discloses antimycotic nail varnish compositions containing an antimycotic agent, a water soluble polymeric film-forming agent selected from hydroxalkyl and carboxyalkyl chitosans, ethyl acetate (as penetration enhancer), cetostearyl alcohol (as plasticizer), ethanol and water.

It has now been surprisingly found that a simpler composition of terbinafine, containing terbinafine as the sole active antimycotic ingredient, together with a low concentration of film forming agent and a proper solvent system, is effective in the treatment of onychomycosis even when it is administered once a week. Furthermore, the composition appears even more effective when it is applied once a day for the first month, then is applied once weekly until the end of treatment.

DESCRIPTION OF THE INVENTION

Figure 1:
FIG. 1 shows batches P-13-008 and P-13-009, having compositions according to the present disclosure, as compared to batches P-13-010 and P-13-011, having compositions according to the prior art, before exposure to 5° C.

An object of the present invention is a method of treating onychomycosis in a patient in need of such a treatment, comprising applying to the affected areas of said patient a composition comprising at least about 9% by weight terbinafine or a pharmaceutically acceptable salt thereof, hydroxypropyl chitosan, a lower alkanol and water, once weekly.

A further object of the present invention is a method of treating onychomycosis in a patient in need of such a treatment, which method comprises applying to the nails of said patient a composition consisting essentially of:
 a) terbinafine and/or at least a pharmaceutically acceptable salt thereof in an amount of from 9 to 11% by weight of the composition,
 b) hydroxypropyl chitosan in an amount of from 0.1 to 0.6% by weight of the composition,
 c) water in an amount of from 10.0 to 40.0% by weight of the composition,
 d) at least a lower alkanol in an amount of from 60 to 80% by weight of the composition.

A further object of the present invention is a novel nail topical composition consisting essentially of:
 a) terbinafine and/or at least a pharmaceutically acceptable salt thereof in an amount from 9 to 11% by weight of the composition,
 b) hydroxypropyl chitosan in an amount from 0.1 to 0.6% by weight of the composition,
 c) water in an amount from 10.0 to 40.0% by weight of the composition,
 d) at least a lower alkanol in an amount from 60 to 80% by weight of the composition.

Moreover, the present invention is directed to the method of treating onychomycosis by administering said composition to the affected area once-weekly for the length of the treatment, which is generally up to one year. Preferably, the weekly administration is preceded by a loading period in which the composition is applied once daily for a period of time from two weeks to up to two months, preferably one month, after which the composition is applied weekly. It has surprisingly been found that with the composition of the present invention there is no need to administer the product once a day throughout the entire treatment period to avoid loss of medication due to nail exposure to water. Thus, a much smaller amount of product needs to be applied during the treatment period. This leads to advantages not only in terms of convenience for the patient, but also in terms of cost of therapy and exposure of the patient and the environment to the chemical agent. Furthermore, the composition according to the present invention does not require the presence of a penetration enhancer in order for the active ingredient to efficiently penetrate into and through the nail plate, as the active ingredient, terbinafine, was found to reach very high concentrations in the nail lamina in both in vitro and in vivo studies.

The composition in accordance to the present invention preferably comprises terbinafine in the form of terbinafine HCl.

The amount of component a) in the composition is in the range from 9 to 11% w/w, preferably 9.5 to 10.5% w/w, and more preferably of about 10% w/w of the total composition.

The composition of the present invention also comprises hydroxypropyl chitosan, namely a water soluble film forming agent, as component b). Film forming agents are by definition (see e.g. DIN 55945 (12/1988)) components of a binder which are essential for forming a film, i.e. a thin layer or cover. The term "water soluble" means in this context that the film forming agent is fully compatible with water so that at 20° C. one part of the film forming agent is soluble in 100 parts or less, preferably 50 parts or less, more preferably 30 parts or less, most preferably 10 parts or less of water.

The amount of the component b) in the range from 0.1 to 0.6% w/w, preferably 0.2 to 0.4% w/w, and more preferably of about 0.3% w/w, of the total composition.

The composition in accordance with the present invention further comprises water as component c). The amount of component c) in accordance with the present invention is from 10 to 40% w/w, preferably from 18 to 30% w/w, more preferably from 18 to 22% of the total composition.

The composition in accordance with the present invention further comprises a lower alkanol or a mixture of lower alkanols as a solvent as component d). The lower alkanol is preferably a $C_1$-$C_4$-alkanol and may be selected from ethanol, propanol, isopropanol, or butanol.

Preferably, the total amount of lower alkanol used in combination with water present in the composition in accordance with the present invention is such to provide acceptable drying times of the formulation once applied to the nails. An acceptable drying time, i.e. the time taken to be dry by touch, is preferably less than about two minutes.

Component d) is usually employed in an amount suitable in order to impart the above noted properties. It is preferred that the component d) be present in the composition in accordance with the present invention in an amount from 60 to 80% w/w, more preferably from 65 to 75% w/w, and even more preferably of about 70% w/w of the total composition.

According to an embodiment of the invention, the composition consists of a) 9.5 to 10.5% by weight terbinafine HCl, b) 0.2 to 0.4% by weight hydroxypropyl chitosan, c) 18 to 30% by weight purified water and d) 65 to 75% by weight ethanol.

According to a further embodiment of the invention, the composition consists of a) about 10% by weight terbinafine HCl, b) about 0.3% by weight hydroxypropyl chitosan, c) about 19.7% by weight purified water and d) about 70% by weight ethanol.

For the purposes of the present invention, the expression "consisting essentially of" means that the claimed composition, in addition to components a), b), c) and d), may optionally contain other excipients and/or adjuvants which, however, should not be present in amounts higher than 8% w/w with respect to the composition; plasticizers and/or penetration enhancers being excluded from such additional optional excipients and/or adjuvants.

According to a further embodiment, the composition of the present invention consists of components a), b), c) and d), whose percentages therefore sum up to 100.

The composition of the present invention is illustrated, but not limited to, the following examples. All amounts in % are w/w %.

EXAMPLE 1

Batches P-13-004, P-13-005, P-13-008 and P-13-009 were prepared following the teaching of the present invention and have the following w/w % compositions:

|  | Batch number | |
| --- | --- | --- |
| Ingredient | P-13-004 P-13-008 | P-13-005 P-13-009 |
| Terbinafine HCl | 5.0 | 10.0 |
| Hydroxypropyl Chitosan | 0.3 | 0.3 |
| Ethanol 96% | 70.0 | 70.0 |
| Water | 24.7 | 19.7 |

Preparation

The formulations are prepared by using a suitable closed vessel provided with a stirrer. To this vessel are added ethanol, water and terbinafine HCl to form a homogeneous mixture. Thereafter, hydroxypropyl chitosan is added and the resulting mixture is stirred until dissolution.

EXAMPLE 2

Comparative

Batches P-13-006, P-13-007, P-13-010 and P-13-011 were prepared following the disclosure of WO02/07683A1 and have the following w/w % compositions:

|  | Batch number | |
| --- | --- | --- |
| Ingredient | P-13-006 P-13-010 | P-13-007 P-13-011 |
| Terbinafine HCl | 5.0 | 10.0 |
| Hydroxypropyl Chitosan | 0.3 | 0.3 |
| Ethanol 96% | 73.0 | 73.0 |
| Water | 16.0 | 11.0 |
| Ethyl Acetate | 4.0 | 4.0 |
| Cetostearyl Alcohol | 1.0 | 1.0 |

Preparation

The formulations are prepared by using a suitable closed vessel provided with a stirrer. To this vessel are added ethanol, ethyl acetate, cetostearyl alcohol, terbinafine HCl and water to form a homogeneous mixture. Thereafter, hydroxypropyl chitosan is added and the resulting mixture is stirred until dissolution.

EXAMPLE 3

The formulations prepared according to Example 1 (batch P-13-008 and batch P-13-009) and those prepared according to Example 2 (batch P-13-010 and batch P-13-011) were stored at prescribed temperatures (5° C. and 10° C.) for at least 1 hour.

Figure 2:
FIG. 2 shows batches P-13-008 and P-13-009, having compositions according to the present disclosure, as compared to batches P-13-010 and P-13-011, having compositions according to the prior art, after exposure to 5° C. for 1 hour.

Pictures of the samples were taken before and after the exposure time at each temperature to evaluate the appearance of the solution and are reported in FIGS. 1 and 2. Observations are summarized in Table 1.

TABLE 1

| Batch number | T = 5° C. | T = 10° C. |
| --- | --- | --- |
| P-13-008 | Clear solution | Clear solution |
| P-13-009 | Clear solution | Clear solution |
| P-13-010 | White flocculate | White flocculate |
| P-13-011 | White flocculate | Opalescent solution |

As it shall be easily appreciated, the solutions of the present invention (batch P-13-008 and batch P-13-009) are superior to the solutions prepared following the disclosure of WO02/07683A1 (batch P-13-010 and batch P-13-011) if exposed to temperatures below 10° C., since no white flocculate is observed. The absence of the white flocculate, allows the formulations prepared following the teaching of the present invention to be transported without the need of a controlled temperature environment during the cold season.

EXAMPLE 4

The formulations prepared according to Example 1 (batch P-13-004 and batch P-13-005) and prepared according to Example 2 (batch P-13-006 and batch P-13-007) were subjected to an accelerated stability study at a temperature higher than 40° C. for one week in a controlled temperature storage chamber to evaluate the technological stability.

Figure 3:
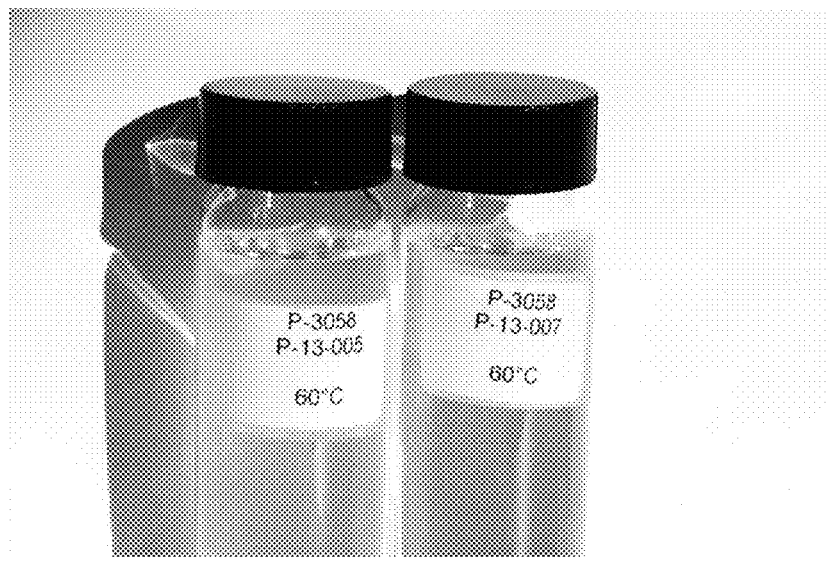
FIG. 3 shows batch P-13-005, having a composition according to the present disclosure, as compared to batch P-13-007, having a composition according to the prior art, after 1 week exposure to a temperature higher than 40° C.
Figure 4:
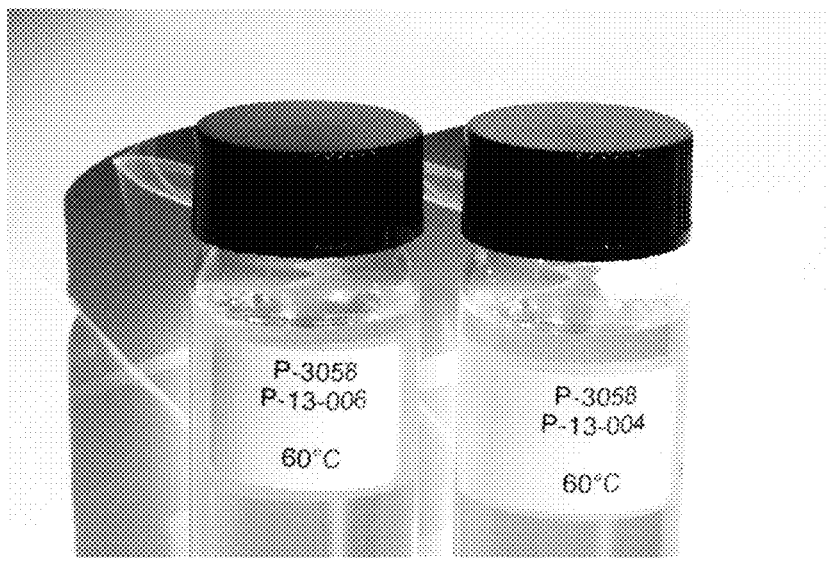
FIG. 4 shows batch P-13-004, having a composition according to the present disclosure, as compared to batch P-13-006, having a composition according to the prior art, after 1 week exposure to a temperature higher than 40° C.

Pictures of the samples, which are reported in FIGS. 3 and 4, were taken before and after the exposure time to evaluate the color of the solution, according to European Pharmacopoeia (monograph 2.2.2, method II, 7$^{th}$ Edition—7.0) for the yellow series (Y) and the brown-yellow series (BY). According to the cited European Pharmacopoeia's monograph, colors of solutions are reported in 7-point scale, where Y1 corresponds to most intense yellow and Y2, Y3 etc. correspond to gradually less intense yellow, where Y7 is least yellow, and no yellow is comparable to water. Similarly, BY1 corresponds to most intense brown yellow and BY7 is less intense brown yellow. No brown yellow is comparable to water. Using identical tubes of colorless, transparent, neutral glass with a flat base and an internal diameter of 15 mm to 25 mm, the liquid to be examined were compared with water or the reference color solution. The colors were compared in diffused daylight, viewing vertically against a white background.

Results are summarized in Table 2.

TABLE 2

| Batch number | t0 | t = 1 week |
|---|---|---|
| P-13-004 | Y7; BY7 | Y7; BY7 |
| P-13-005 | Y7; BY7 | Y7; BY7 |
| P-13-006 | Y7; BY7 | Y6; BY6 |
| P-13-007 | Y7; BY7 | Y5; BY5 |

Conclusions. The solutions prepared following the teaching of the present invention (batch P-13-004 and batch P-13-005) are superior to the solutions prepared following the disclosure of WO02/07683A1 (batch P-13-006 and batch P-13-007) if exposed to a temperature higher than 40° C., since no discoloration is observed. The absence of the discoloration allows the formulations prepared following the teaching of the present invention to avoid the need to be stored at controlled temperature.

EXAMPLE 5

Nail lacquer formulations having the following compositions by weight are prepared:

| | terbinafine HCl | | | | | |
|---|---|---|---|---|---|---|
| | 1% | 2% | 4% | 5% | 8% | 10.0% |
| hydroxypropyl chitosan | 0.3% | 0.3% | 0.3% | 0.3% | 0.3% | 0.3% |
| purified water | 28.7% | 27.7% | 25.7% | 24.7% | 21.7% | 19.7% |
| ethanol | 70.0% | 70.0% | 70.0% | 70.0% | 70.0% | 70.0% |

The formulations are prepared by using a suitable closed vessel provided with a stirrer. To this vessel are added ethanol, deionized water and terbinafine HCl to form a mixture. Thereafter, hydroxypropyl chitosan is added and the resulting mixture is stirred until dissolution.

The obtained nail lacquer compositions have a clear and homogeneous appearance and are perfectly transparent and colorless even after prolonged storage.

EXAMPLE 6

In Vitro Activity

An in vitro experimental onychomycosis study was designed to assess the preventive and curative activity of the compositions containing terbinafine HCl 1%, 4% and 8% as per the Example 5. The compositions were compared to untreated control and to a placebo. *Trichophyton rubrum*, *Trichophyton mentagrophytes* var. *interdigitale* (2 strains) and *Microsporum canis* clinical isolates were used as test organisms. Bovine hoof slices from animals of either sex, aged 8-12 months were used as human nail models. To assess the onychomycosis preventive activity of the compositions, 70 μm thick bovine nail fragments, previously immersed in the different antifungal formulations and left to dry in the air, were inserted into the agar medium of Petri dishes inoculated with the clinical isolates and incubated up to 21 days, with weekly observations and weekly transplant into sterile plates for growth confirmation. To assess the onychomycosis curative activity of the compositions, 120 μm thick bovine nail fragments were inserted in plates previously inoculated with the clinical isolates and incubated up to 21 days. Nails covered by mycelium were then either treated with the different formulations and with the placebo or left untreated, transferred to sterile agar medium plates and incubated up to 21 days with weekly observation. The results obtained in the study demonstrated that full and sustained growth of fungi was obtained in negative control and placebo treated nails. The application of the 1%, 4% and 8% compositions on the non-infected nails was able to prevent fungal growth (Table 3). No fungal growth was observed in nails covered by mycelium and subsequently treated with the compositions containing terbinafine HCl 1%, 4% and 8% as per the Example 5 at all tested concentrations, demonstrating also a curative activity of the product (Table 4).

TABLE 3

In Vitro Preventive activity of the compositions containing terbinafine HCl 1%, 4% and 8% as per the Example 5 in an experimental in vitro onychomycosis model

| SUBSTANCE | STRAIN | MEAN RING° (mm) AFTER DAYS | | | | | | | GROWTH AFTER TRANSPLANT ON DAY | | |
|---|---|---|---|---|---|---|---|---|---|---|---|
| | | 3 | 6 | 9 | 12 | 15 | 18 | 21 | 7* | 14* | 21* |
| Terbinafine HCl 1% | T. mentagrophytes | 24 | 24 | 7 | 0 | 0 | 0 | 0 | − | − | − |
| | T. mentagrophytes | > | > | > | > | > | > | > | − | − | − |
| | T. rubrum | > | > | > | > | > | > | > | − | − | − |
| | M. canis | > | > | > | > | > | > | > | − | − | − |
| Terbinafine HCl 4% | T. mentagrophytes | 26 | 28 | 16 | 12 | 10 | 8 | 5 | − | − | − |
| | T. mentagrophytes | > | > | > | > | > | > | > | − | − | − |
| | T. rubrum | > | > | > | > | > | > | > | − | − | − |
| | M. canis | > | > | > | > | > | > | > | − | − | − |
| Terbinafine HCl 8% | T. mentagrophytes | 37 | 36 | 29 | 28 | 25 | 23 | 23 | − | − | − |
| | T. mentagrophytes | > | > | > | > | > | > | > | − | − | − |
| | T. rubrum | > | > | > | > | > | > | > | − | − | − |
| | M. canis | > | > | > | > | > | > | > | − | − | − |

TABLE 3-continued

In Vitro Preventive activity of the compositions
containing terbinafine HCl 1%, 4% and 8% as per the Example
5 in an experimental in vitro onychomycosis model

| SUBSTANCE | STRAIN | MEAN RING° (mm) AFTER DAYS | | | | | | | GROWTH AFTER TRANSPLANT ON DAY | | |
|---|---|---|---|---|---|---|---|---|---|---|---|
| | | 3 | 6 | 9 | 12 | 15 | 18 | 21 | 7* | 14* | 21* |
| Untreated | T. mentagrophytes | 0 | 0 | 0 | 0 | 0 | 0 | 0 | + | + | + |
| Control | T. mentagrophytes | 0 | 0 | 0 | 0 | 0 | 0 | 0 | + | + | + |
| | T. rubrum | 0 | 0 | 0 | 0 | 0 | 0 | 0 | + | + | + |
| | M. canis | 0 | 0 | 0 | 0 | 0 | 0 | 0 | + | + | + |
| Placebo | T. mentagrophytes | 0 | 0 | 0 | 0 | 0 | 0 | 0 | + | + | + |
| | T. mentagrophytes | 0 | 0 | 0 | 0 | 0 | 0 | 0 | + | + | + |
| | T. rubrum | 0 | 0 | 0 | 0 | 0 | 0 | 0 | + | + | + |
| | M. canis | 0 | 0 | 0 | 0 | 0 | 0 | 0 | + | + | + |

°= mean of 4 values
+ = growth;
− = no growth
> = ring greater than 40 mm
*the presence or absence of fungal growth was assessed 3 weeks after transplant

TABLE 4

In Vitro Curative activity of the compositions
containing terbinafine HCl 1%, 4% and 8% as per the Example
5 in an experimental in vitro onychomycosis model

| SUBSTANCE | STRAIN | Withdrawal of untreated nail after weeks: | | | | | | | | |
|---|---|---|---|---|---|---|---|---|---|---|
| | | 1 Growth* after days | | | 2 Growth* after days | | | 3 Growth* after days | | |
| | | 7 | 14 | 21 | 7 | 14 | 21 | 7 | 14 | 21 |
| Terbinafine | T. mentagrophytes | − | − | − | − | − | − | − | − | − |
| HCl | T. mentagrophytes | − | − | − | − | − | − | − | − | − |
| 1% | T. rubrum | − | − | − | − | − | − | − | − | − |
| | M. canis | − | − | − | − | − | − | − | − | − |
| Terbinafine | T. mentagrophytes | − | − | − | − | − | − | − | − | − |
| HCl | T. mentagrophytes | − | − | − | − | − | − | − | − | − |
| 4% | T. rubrum | − | − | − | − | − | − | − | − | − |
| | M. canis | − | − | − | − | − | − | − | − | − |
| Terbinafine | T. mentagrophytes | − | − | − | − | − | − | − | − | − |
| HCl 8% | T. mentagrophytes | − | − | − | − | − | − | − | − | − |
| | T. rubrum | − | − | − | − | − | − | − | − | − |
| | M. canis | − | − | − | − | − | − | − | − | − |
| Untreated | T. mentagrophytes | + | + | + | + | + | + | + | + | + |
| Control | T. mentagrophytes | + | + | + | + | + | + | + | + | + |
| | T. rubrum | + | + | + | + | + | + | + | + | + |
| | M. canis | + | + | + | + | + | + | + | + | + |
| Placebo | T. mentagrophytes | − | + | + | + | + | + | + | + | + |
| | T. mentagrophytes | − | + | + | + | + | + | + | + | + |
| | T. rubrum | + | + | + | + | + | + | + | + | + |
| | M. canis | + | + | + | + | + | + | + | + | + |

*fungal growth in the nail treated

EXAMPLE 7

Clinical Results—Once Weekly Topical Administration

An efficacy evaluation was carried out on patients with mild-to-moderate onychomycosis due to dermatophytes treated with the compositions described in the present invention. The patients were randomized in three groups, treated in parallel for 24 weeks with the 10% or 5% terbinafine HCl compositions of the Example 5. The 10% terbinafine HCl composition was applied once daily (10% o.d., n=19) or once weekly (10% o.w., n=20), and the 5% terbinafine HCl composition was applied once daily (5% o.d., n=18). The efficacy was measured in terms of decrease of affected nail area at the end of treatment versus baseline and the results were compared with those of a group given the composition of the Example 5, containing a lower concentration of terbinafine HCl (1-2%, n=31).

Overall, 88 patients were included in the efficacy analysis. The investigation was aimed at comparing the decrease of affected nail area between 1-2% o.d. and 5% o.d., 10% o.d., 10% o.w. pooled together. A further objective was to evaluate which dose regimen was the most effective.

Images of affected toenail area were evaluated by a Blinded Independent Investigator and planimetry measured by a computerized imaging analysis. The proportion of affected nail area/total nail area at the different time points was chosen as parameter of efficacy.

The proportion of affected nail area was lowered by 11.1% at end of treatment versus baseline in the pooled group of patients given the 5 and 10% terbinafine HCl compositions, while no effect was noticed in the 1-2% o.d. treatment group of (+2.4%), the difference being statistically significant (p=0.001, ANCOVA).

In addition, a pairwise comparison analysis was carried out among the different dose regimens. A statistically significant interaction between dose regimens in decreasing the affected nail area was observed after 24 wks: the difference was statistically significant between 10% o.w. and 1-2% o.d. (−12.8% vs+2.4%, p=0.0383) and between 5% o.d. and 1-2% o.d. (−11.1% vs+2.4%, p=0.0254). The difference between 10% o.d. and 1-2% o.d. (−9.7% vs+2.4%) was not significant. These results indicate that the compositions of the Example 1 with higher concentrations of terbinafine HCl were superior to that at lower concentration in terms of efficacy in the treatment of onychomycosis. Surprisingly, the best results were obtained when the composition having a 10% content of terbinafine HCl was applied once weekly.

EXAMPLE 8

Dermal Tolerability in Rats

Two nail lacquer formulations having the following compositions by weight were prepared:

| Ingredient | Composition A | Composition B |
| --- | --- | --- |
| terbinafine HCl | 10.0% | 15.0% |
| hydroxypropyl chitosan | 0.3% | 2.0% |
| purified water | 19.7% | 13.0% |
| ethanol | 70.0% | 70.0% |

Dermal tolerability of the two compositions was investigated in rats of both sexes in two identical 28-day studies. The product was daily applied and covered by a semi-occlusive dressing and left for a 6-hour exposure period. The procedure was repeated daily during the 28 days.

Tolerability was examined in terms of appearance and severity of dermal changes.

Following application of composition A, containing 10% terbinafine and 0.3% hydroxypropyl chitosan, just few and mild local dermal adverse findings (reddening, scabs and scaling) were noticed.

Following application of composition B, containing 15% terbinafine HCl and 2.0% hydroxypropyl chitosan, the following local adverse effects were noticed: ulcers/erosions, scab formation, epithelial hyperplasia, inflammatory cell infiltrates, fibrosis and parakeratosis, with increased severity and rate in female animals.

In conclusion, composition A was better tolerated in animal testing compared to composition B.

EXAMPLE 9

Accelerated Stability

The formulations prepared according to the teaching of the present invention as per the Example 1 (batch P-13-004 and batch P-13-005) and the formulations prepared following the disclosure of WO02/07683A1 as per the Example 2 (batch P-13-006 and batch P-13-007) were subjected to an accelerated stability study at a temperature higher than 40° C. for one week in a controlled temperature storage chamber to evaluate the technological stability.

Viscosity was determined using a suspended level viscometer size number 1, according to European Pharmacopoeia (7th edition, monograph 2.2.9), at a temperature of 25±0.1° C.

The suspended level viscometer was filled as described in the cited reference using an appropriate liquid quantity (approx. 17 mL).

The time required for the level of the liquid to drop from the mark E to the mark F was measured with a stop-watch; the average of three readings was used as the flow time of the liquid to be examined.

The kinematic viscosity η, expressed in millipascal× seconds (mPas) was calculated using the formula:

$$v = kt$$

where
k=constant of the viscometer, expressed in square millimeters per second squared and determined using a suitable viscometer calibration liquid
t=flow time, in seconds, of the liquid to be examined.

Kinematic viscosity data collected at the starting point (t0, i.e. before exposure to a temperature higher than 40° C.) were compared with the data obtained after 2 weeks of exposure at a temperature higher than 40° C. in terms of % difference.

For the purpose of this invention, an acceptable loss of viscosity means that the viscosity % difference, calculated with reference to the starting point, should not exceed the value of 10%.

Results are summarized in Table 5.

TABLE 5

| | Kinematic viscosity (mPas) | | |
| --- | --- | --- | --- |
| Batch number | t0 | t = 2 weeks | % difference |
| P-13-004 | 375.17 | 353.40 | −5.8036 |
| P-13-005 | 396.37 | 363.75 | −8.2305 |
| P-13-006 | 645.40 | 558.64 | −13.443 |
| P-13-007 | 650.07 | 557.67 | −14.213 |

Conclusions. The formulations prepared following the teaching of the present invention (batch P-13-004 and batch P-13-005) are superior to the formulations prepared following the disclosure of WO02/07683A1 (batch P-13-006 and batch P-13-007) if exposed to a temperature higher than 40° C., since an acceptable loss of viscosity is observed.

The observed acceptable loss of viscosity leads to a superior technological stability.

EXAMPLE 10

Drying Time

The formulations prepared according to the teaching of the present invention as per the Example 1 (batch P-13-004 and batch P-13-005) and the formulations prepared following the disclosure of WO02/07683A1 as per the Example 2 (batch P-13-006 and batch P-13-007) were compared to evaluate the drying time once applied on the nails, i.e. the time taken by the solvent to evaporate to leave a dry surface. Evaporation time was calculated by measuring the weight loss over time of a glass slide following application of a given quantity of the formulation on a given surface, realized through a plastic hedge applied on the glass. Five microliters of formulation were applied on 2 cm² surface. Experiments were carried out at room temperature. Three measurements were taken for each batch and the mean value was used for the calculation. Evaporation time was reached when at least 80% of the start weight was lost. Results are summarized in Table 6.

TABLE 6 evaporation time

| Batch number | Evaporation time (seconds) |
|---|---|
| P-13-004 | 65 |
| P-13-005 | 70 |
| P-13-006 | 145 |
| P-13-007 | 100 |

From the results above the formulations of the present invention (batch P-13-004 and batch P-13-005) are superior to the formulations prepared following the disclosure of WO02/07683A1 (batch P-13-006 and batch P-13-007) in that the drying time is shorter, thus realizing a user-friendly way of application: the user needs to wait a short time to let the formulation dry before using his/her hands/feet in usual daily operations.

EXAMPLE 11

Clinical Results Once Weekly Topical Administration with Loading Period

A multicentre, randomized, double-blind within frequency of administration, vehicle controlled, dose-finding, parallel-group study was completed in patients with mild-to-moderate dermatophyte onychomycosis (distal lateral subungual onychomycosis, defined as 25%-60% clinical involvement of the target toenail, without dermatophytomas or matrix/lunula involvement) randomized to apply for 52 weeks one of the following treatment regimens:
1) 10% terbinafine HCl once daily as per the Example 1 for the whole treatment length (P-3058 10% o.d., n=93),
2) 10% terbinafine once daily as per the Example 1 for the first month, followed by 10% terbinafine once weekly until the end of treatment period, (P-3058 10% o.w., n=91),
3) 5% terbinafine HCl once daily as per the Example 1 (P-3058 5% o.d., n=94),
4) vehicle, not containing any terbinafine nor any other antifungal agent (n=92:58 o.d. and 34 o.w.).

The treatment period was followed by 24-weeks of follow-up. The investigation was aimed at evaluating the effect of the different doses of the investigational product P-3058 compared to the vehicle in the treatment of onychomycosis at the end of follow-up (week 76).

The primary efficacy endpoint was the proportion of patients achieving "Responder rate" at the end of the wash-out period (week 76), defined as composite parameter of ≤10% clinical involvement of the target toenail and mycological cure (negative microscopic KOH examination and negative culture). The key secondary efficacy endpoint was the proportion of patients achieving "Complete cure" defined as composite parameter of 0% clinical involvement of the target toenail and mycological cure (negative microscopic KOH examination and negative culture) at different time points during the treatment phase as well as during the wash-out period.

Overall, 370 patients were included in the efficacy analysis (MITT population). At baseline, the percentage of the affected target toenail area was in average 40.7% (min: 14, max: 70).

The results were as follows: concerning primary efficacy endpoint, at the end of follow-up (week 76), the rate of responder patients were: 16.13% in P-3058 10% o.d., 15.96% in P-3058 5% o.d., 23.08% in P-3058 10% o.w., 20.65% in vehicle group. As far as the key secondary efficacy endpoint was concerned, at the end of follow-up (week 76), the rates of complete cured patients were: 8.6% in P-3058 10% o.d., 7.45% in P-3058 5% o.d., 10.99% in P-3058 10% o.w., 6.52% in vehicle group.

Surprisingly, both in the primary and in the secondary efficacy endpoints the group of patients treated by the composition of 10% terbinafine o.w. according to the present invention had the highest rate of success compared to both the 10% and 5% o.d. treatment regimens.

The invention claimed is:
1. A composition comprising:
   a) terbinafine HCl in an amount of from about 9% to about 10% by weight of the composition;
   b) hydroxypropyl chitosan in an amount of about 0.3% by weight of the composition;
   c) water in an amount of from about 19.7% to about 24.7% by weight of the composition; and
   d) ethanol in an amount of about 70% by weight of the composition;
wherein the composition does not include plasticizers and/or penetration enhancers.
2. The composition of claim 1 wherein the composition consists of:
   a) terbinafine HCl in an amount of from 9.5% to 10% by weight of the composition;
   b) hydroxypropyl chitosan in an amount of 0.3% by weight of the composition;
   c) water in an amount of from 19.7% to 24.7% by weight of the composition; and
   d) ethanol in an amount of 70% by weight of the composition.
3. The composition of claim 1 wherein the composition consists of:
   a) terbinafine HCl in an amount of about 10% by weight of the composition;
   b) hydroxypropyl chitosan in an amount of about 0.3% by weight of the composition;
   c) water in an amount of about 19.7% by weight of the composition; and
   d) ethanol in an amount of about 70% by weight of the composition.
4. The composition of claim 1 wherein the composition is a nail lacquer.

* * * * *

UNITED STATES PATENT AND TRADEMARK OFFICE
CERTIFICATE OF CORRECTION

PATENT NO. : 10,172,811 B2
APPLICATION NO. : 14/765964
DATED : January 8, 2019
INVENTOR(S) : Federico Mailland et al.

Page 1 of 1

It is certified that error appears in the above-identified patent and that said Letters Patent is hereby corrected as shown below:

On the Title Page

Column 1, item (87), "PCT Pub. Date: Aug. 4, 2014" should read --PCT Pub. Date: Aug. 14, 2014--.

Signed and Sealed this
Nineteenth Day of March, 2019

Andrei Iancu
*Director of the United States Patent and Trademark Office*